United States Patent
Cohen

(10) Patent No.: US 6,757,559 B2
(45) Date of Patent: Jun. 29, 2004

(54) SYSTEM FOR AND METHOD OF DETECTING POLYGRAPH COUNTERMEASURES

(75) Inventor: Emmanuel Cohen, Jerusalem (IL)

(73) Assignee: Amitronix Inc., Jerusalem (IL)

( * ) Notice: Subject to any disclaimer, the term of this patent is extended or adjusted under 35 U.S.C. 154(b) by 83 days.

(21) Appl. No.: 10/040,760

(22) Filed: Jan. 9, 2002

(65) Prior Publication Data

US 2002/0091336 A1 Jul. 11, 2002

Related U.S. Application Data

(60) Provisional application No. 60/260,530, filed on Jan. 10, 2001.

(51) Int. Cl.[7] ................................................. A61B 5/05
(52) U.S. Cl. ....................................................... 600/547
(58) Field of Search ................................ 600/547, 300, 600/544, 545, 510, 523; 346/33 R, 13; 324/76.13

(56) References Cited

U.S. PATENT DOCUMENTS

| | | | | |
|---|---|---|---|---|
| 3,971,034 A | * | 7/1976 | Bell et al. | 346/33 R |
| 5,406,956 A | * | 4/1995 | Farwell | 600/544 |
| 5,876,334 A | * | 3/1999 | Levy | 600/300 |

* cited by examiner

*Primary Examiner*—Mary Beth Jones
*Assistant Examiner*—Brian Scott Szmal
(74) *Attorney, Agent, or Firm*—Mark M. Friedman

(57) ABSTRACT

A system for, and method of identifying a use of countermeasures by a subject of a polygraph test, the method including the steps of: (a) posing a plurality of questions to the subject; (b) determining, for each question, a time interval between an end of the question and a start of an answer by the subject to the question, thereby generating a plurality of time intervals, and (c) comparing the time intervals to identify the countermeasures.

19 Claims, 3 Drawing Sheets

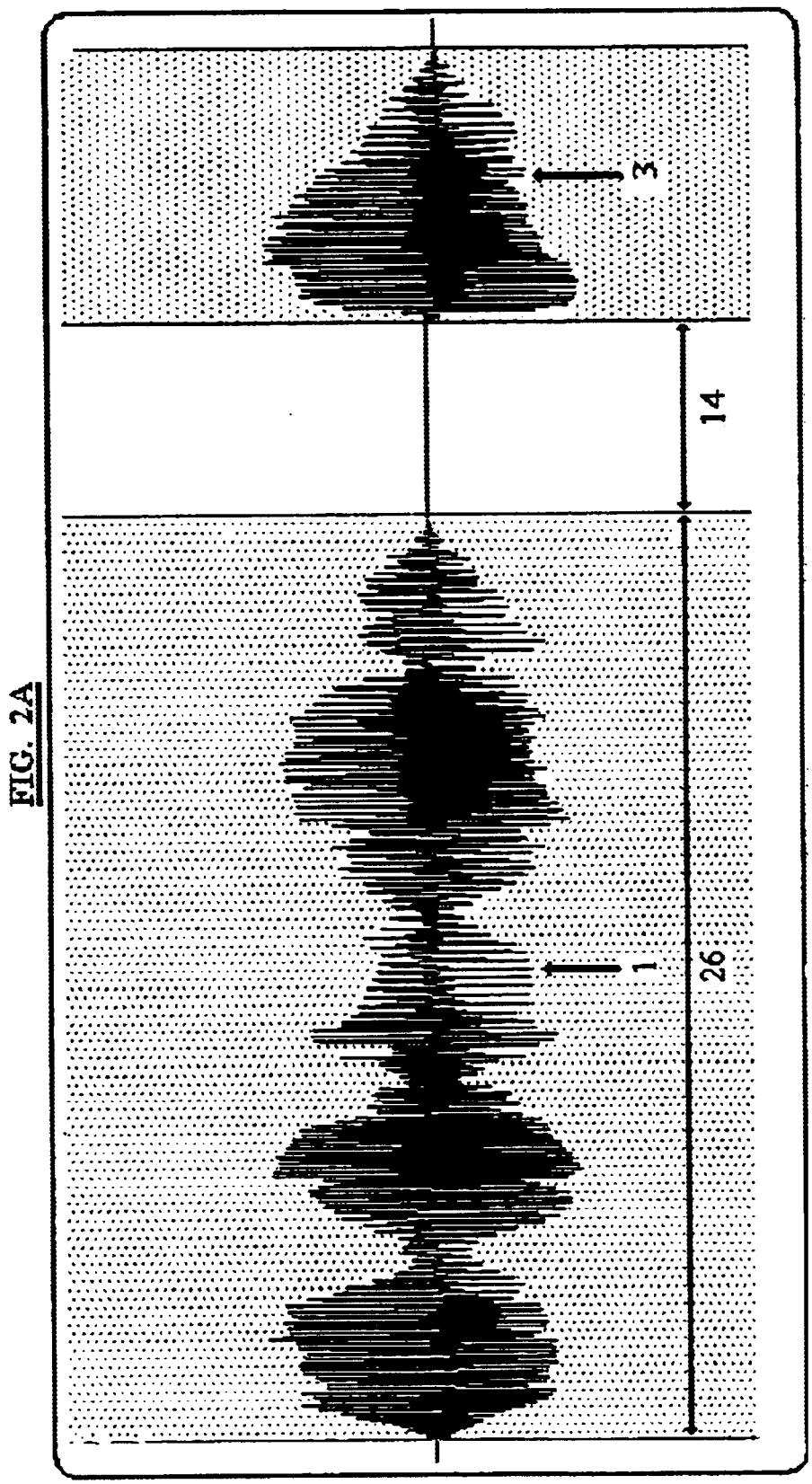

SYSTEM FOR AND METHOD OF DETECTING POLYGRAPH COUNTERMEASURES

This patent application draws priority from my U.S. Provisional Patent Application, Serial No. 60/260,530 filed Jan. 10, 2001.

FIELD AND BACKGROUND OF THE INVENTION

The present invention relates to polygraph examinations and, in particular, it concerns a system of and a method for detecting polygraph countermeasures.

A polygraph examination utilizes a polygraph instrument that collects physiological data from at least three systems in the human body. Tubes and leads are placed over the examinee's chest and abdominal area to monitor respiratory activity. Two small metal plates, attached to the fingers, are used to monitor sweat gland activity. A blood pressure cuff, or similar device, monitors cardiovascular activity.

A typical polygraph examination is composed of three periods referred to as a pre-test, a chart collection phase and a test data analysis phase. In the pre-test, the polygraph examiner completes required paperwork and talks with the examinee about the test. During this period, the examiner discusses the questions to be asked and familiarizes the examinee with the testing procedure. During the chart collection phase, the examiner administers and collects a number of polygraph charts. The examiner subsequently analyzes the charts and renders his opinion as to the truthfulness of the person taking the test. The examiner, when appropriate, offers the examinee an opportunity to explain physiological responses in relation to one or more questions asked during the test.

However, some deceptive subjects use deliberate techniques in attempt to appear non-deceptive while the polygraph is monitoring their psycho-physiological responses.

There are two particularly problematic types of countermeasures:

Physical countermeasures involve the use of physical means to prompt a response, e.g., biting the tongue, constricting anal muscles, pressing toes against the floor (or against a sharp object within a shoe), etc.

Mental countermeasures involve the use of thoughts that are stimulating, disturbing, engaging, e.g., an arousing thought or a difficult mathematical calculation.

There are elaborate polygraph countermeasures that are taught by major intelligence agencies and also on Internet web sites (one of which is antipolygraph.org) aimed to manipulate the polygraph chart record.

Most polygraph tests are of the CQT variety, in which deception is determined by comparing physiological responses to relevant questions to a baseline determined by control questions. Using countermeasures as described above, it is possible to achieve a response level to the control questions that is greater than the response level to the relevant questions, in which case a "Non-Deception Indicated" result is obtained. In some cases, the response level to the relevant questions is similar to the response level to the control questions, in which case the test results are inconclusive.

Thus, although countermeasure means for beating the polygraph examination are effective and readily available, there exists no effective, systematic method of exposing the use of countermeasures, particularly when such countermeasures are used in a professional manner. There is therefore a recognized need for, and it would be highly advantageous to have, a method of and a system for exposing the use of polygraph test countermeasures. It would be of further advantage for such a method and system to be implementable in existing polygraph systems.

SUMMARY OF THE INVENTION

According to one aspect of the present invention, there is provided a system for detecting the use of countermeasures by a subject of a polygraph test, the system including: (a) a polygraph instrument for recording at least one physiological activity of the subject; (b) a sound recording device for recording audio data during the polygraph test; and (c) means for measuring time, operatively connected to the sound recording device.

According to another aspect of the present invention, there is provided a method for identifying a use of countermeasures by a subject of a polygraph test, the method including the steps of: (a) posing a plurality of questions to the subject; (b) determining, for each question, a time interval between an end of the question and a start of an answer by the subject to the question, thereby generating a plurality of time intervals, and (c) comparing the time intervals to identify the countermeasures.

According to further features in the described preferred embodiments, the questions include control questions and relevant questions.

According to further features in the described preferred embodiments, the method further includes the step of: (d) monitoring at least one physiological response of the subject.

According to still further features in the described preferred embodiments, the method further includes the step of: (d) displaying sound waves of the answer.

According to further features in the described preferred embodiments, the posing of the questions transpires during the polygraph test.

According to further features in the described preferred embodiments, the answer is a sound response.

According to still further features in the described preferred embodiments, the method further includes the step of: (d) recording a sound recording of the question and the answer.

According to still further features in the described preferred embodiments, in the comparing of the time intervals, $X_C$ represents an average of the time intervals pertaining to the control questions, and $X_R$ represents an average of the time intervals pertaining to the relevant questions, the use of countermeasures by the subject being indicated when a difference between $X_C$ and $X_R$ exceeds a predetermined value.

According to still further features in the described preferred embodiments, in the comparing of the time intervals, the use of countermeasures by the subject is indicated when $X_R - X_C > \delta_1$ or when $X_C - X_R > \delta_2$.

According to still further features in the described preferred embodiments, No Deception Indicated (NDI) is concluded when a difference between $X_C$ and $X_R$ is below a pre-determined value.

According to still further features in the described preferred embodiments, the system further includes: (d) processing means operatively connected to the sound recording device polygraph machine and to the means for measuring time, wherein the processing means for producing time information is associated with the audio data.

According to still further features in the described preferred embodiments, the processing means are designed and configured for identifying use of countermeasures by the subject.

According to still further features in the described preferred embodiments, the processing means are designed and configured for identifying use of countermeasures by the subject based on the time information.

According to still further features in the described preferred embodiments, the processing means are designed and configured for identifying use of countermeasures so as to: (i) calculate for each question of a plurality of questions, a time interval between an end of the question and a start of an answer by the subject to the question, thereby generating a plurality of time intervals, and (ii) compare the time intervals to identify the countermeasures.

According to still further features in the described preferred embodiments, the at least one physiological activity is monitored using galvanic skin response (GSR).

According to still further features in the described preferred embodiments, the processing means are designed and configured to utilize the time information so as to: (i) calculate for each question of a plurality of questions, a time interval between a beginning of the question and a time corresponding to a minimum value adjacent to a galvanic skin response peak to the question, thereby generating a plurality of time intervals, and (ii) compare the time intervals to identify the countermeasures.

According to still further features in the described preferred embodiments, the system further includes: (d) means for displaying the audio data in a graphic form.

According to still further features in the described preferred embodiments, the system further includes: (d) means for displaying the audio data as a function of time.

According to still further features in the described preferred embodiments, the time intervals include control question time intervals and relevant question time intervals, the control question time intervals being compared with the relevant question time intervals.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2A is a detail view of FIG. 1 illustrating an audio output composed of a control question and a control answer.

DESCRIPTION OF THE PREFERRED EMBODIMENTS

Figure 1:
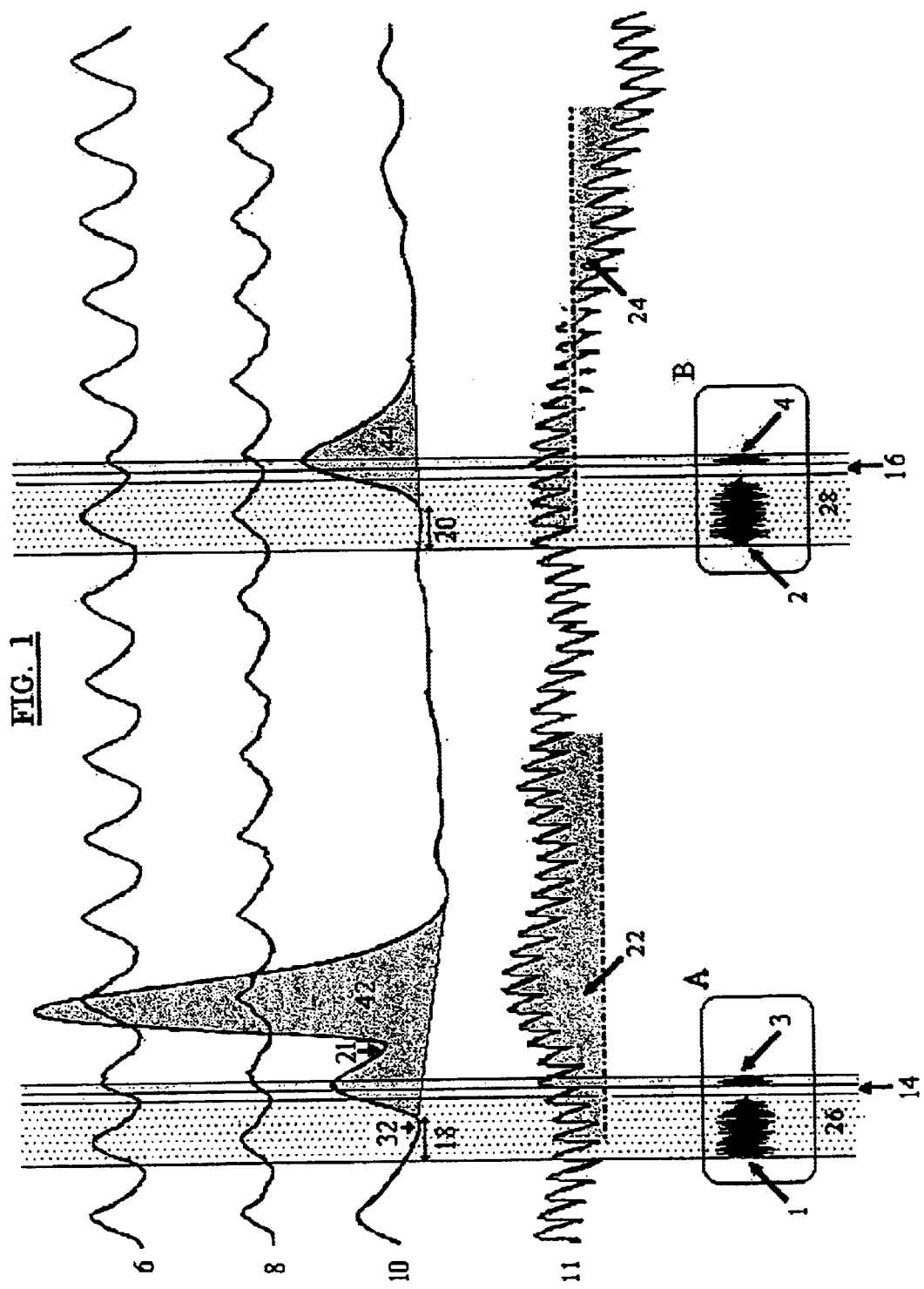
FIG. 1 illustrates a polygraph chart with an audio output displayed according to one embodiment of the present invention.

The principles of the countermeasure detection method according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

As used herein, the term "polygraph" refers to any kind of lie detector, and most typically, to an instrument for recording physiological phenomena such as blood pressure, pulse rate, and respiration of a human subject as the subject listens and responds to questions put to him by an operator. The recorded data are then used as the basis for making a judgment as to whether or not the subject is lying.

The present invention is a method of and a system for improving the reliability of polygraph examinations by exposing the use of polygraph test countermeasures.

According to the teachings of the present invention there is provided a system that records audio readings along with the physiological readings (chest breathing, diaphragm breathing, blood pressure, pulse rate, electrical conductivity, etc.) of a conventional polygraph. FIG. 1 illustrates a chart of these parameters. The parameters are plotted as a graph, wherein the X-axis represents time and the Y-axis represents signal amplitude. An abdominal parameter 6 corresponds to stomach movements during inhalation-exhalation cycles. A thoracic parameter 8 corresponds to chest movements during the inhalation-exhalation cycles. A galvanic skin parameter 10 corresponds to changes in the skin electrical conductivity. Blood pressure is represented by a graph 11.

During a conventional polygraph test, a subject (examinee) is asked a series of questions that include control and relevant questions. A control question is a question to which the subject will lie, or at the very least, a question that elicits a disturbance in the subject. A typical control question might be: "Have you ever stolen prior to working for this company?" Irrelevant questions, based on true and obvious statements of fact are also asked, e.g., the name and address of the subject, known facts in the life of the subject. Thus, during a particular control question that lasts a time interval 26, the polygraph detects and records a galvanic skin response 12 and a change 22 in the blood pressure of the subject.

When relevant questions are asked during a time interval 28, the polygraph detects and records a response 14 in the skin electrical conductivity and a response 24 in the blood pressure of the subject. Responses in parameters 6 and 8, amplitudes, lengths or total areas of the relevant question response peaks, 14 and 24, are compared to amplitudes, lengths or total areas of control question response peaks, 12 and 22, and a determination is made regarding the truthfulness of the subject.

However, a subject employing well-exercised countermeasure techniques may successfully increase response to control questions, to the point that the response is at least as high or higher than the response to relevant questions, such that usable data is obscured, and the polygraph test is defeated.

Figure 2B:
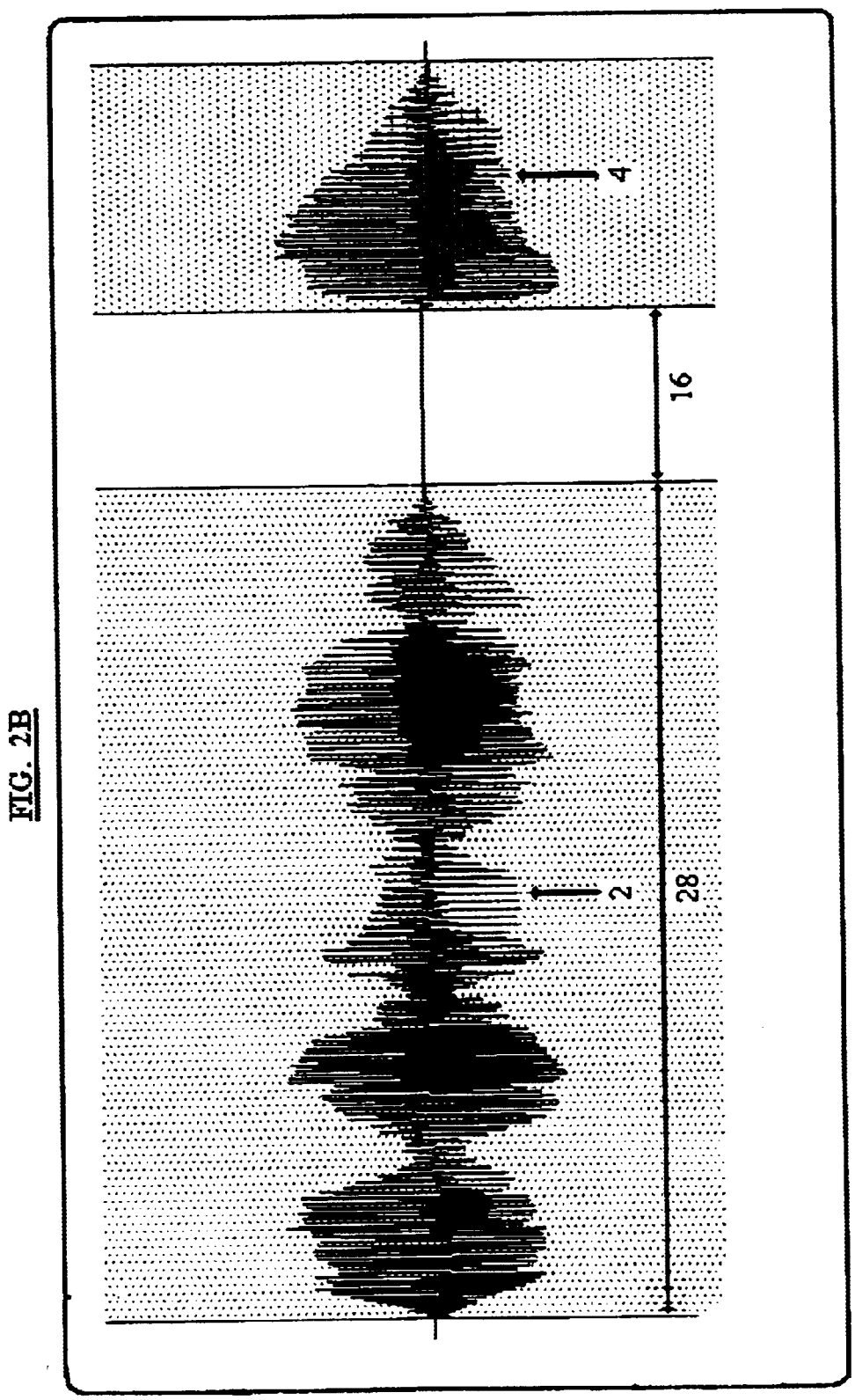
FIG. 2B is a detail view of FIG. 1 illustrating an audio output composed of a relevant question and a relevant answer.

Use of polygraph countermeasures can be detected by utilizing the method in the present invention. In one embodiment of the present invention, an audio output is recorded as shown in views A and B of FIG. 1, which are magnified in FIGS. 2A and 2B, respectively. The audio output includes sound recordings made during the polygraph test. The sound recordings can contain questions, answers to questions, or an absence of sound, such as a pause after a question and before an answer. FIG. 1 shows sound patterns of questions 1 and 2, intervals 14 and 16, and answers 3 and 4.

When administered in a series of control and relevant question and answer groups, an average $X_C$ of time intervals 14 during the control question-answer groups, and an average $X_R$ of time intervals 16 of the relevant question-answer groups are calculated. If the subject employs one or more countermeasure, physical and/or mental, the various techniques characteristically result in changes in the response time by the subject, thereby producing a measurable difference between the times (or some form of averaged time) the subject takes to answer control questions and the times (or some form of averaged time) the subject takes to answer relevant questions, therefore, $X_C \neq X_R$. This may be represented as:

$$|X_R - X_C \oplus > \delta,$$

where $\delta$ is a pre-determined value based on empirical and/or statistical data. Alternatively, the use of countermeasures can be indicated by:

$$X_R - X_C > \delta_1 \text{ or}$$

$$X_C - X_R > \delta_2,$$

where $\delta_1$ and $\delta_2$ are distinct predetermined values.

Similarly, a plurality of pre-determined values can be used to provide a quantitative, probabilistic evaluation of the use of countermeasures.

In the event that the subject does not resort to countermeasures, there is typically no marked difference in time intervals 14 and 16, and, similarly there is no marked difference between averages $X_C$ and $X_R$, such that $X_C \approx X_R$, or $X_R - X_C$ is less than a pre-determined value. In such a case a No Countermeasures Indicated (NCI) conclusion is forthcoming.

In another preferred embodiment of the present invention, the onset of various physiological phenomena in the subject, in response to a question, can be used to identify the use of countermeasures. More specifically, the timing of the galvanic skin response (GSR) has been found to be of particular value in countermeasure identification. In FIG. 1, time interval 18 represents the time elapsed between the beginning of a control question and a beginning 32 of a control question GSR peak 42. The galvanic skin response is preferably associated with the beginning of the question, since the stress of the subject characteristically begins to develop upon hearing the beginning of the question, especially in view of the fact that in standard lie detection procedures, the questions are well known to the subject ahead of time. The GSR may include a peak that begins to develop even prior to the end of the question, as shown in the control question of FIG. 1, such that time interval 18 is smaller than time interval 26.

Moreover, it has been found that interval 18 and a similarly-defined time interval 20 for a relevant question (having a relevant GSR peak 44) are of characteristically different lengths. Hence, the use of countermeasures can be indicated by:

$$t_R - t_C > \delta_3 \text{ or}$$

$$t_C - t_R > \delta_4,$$

wherein $t_R$ represents relevant question time interval 20 (or some average of relevant question time intervals), $t_C$ represents control question time interval 18 (or some average of control question time intervals), and 63 and 64 are predetermined values.

It should be emphasized that countermeasure users, particularly mental countermeasure users, can try to defeat this inventive countermeasure identification approach by practicing mental countermeasures after the natural GSR to the question has been made, so as to artificially increase the magnitude of the GSR to the control question, without changing the characteristic time for interval 18. However, this additional ploy may also be identified by the countermeasure identification method of the instant invention, by defining the end of interval 18 to be any minimum value 21 or 32 in control question GSR peak 42 (the minimum value defined to include local minimum values such as local minimum value 21).

EXAMPLE

Reference is now made to the following example, which together with the above description, illustrates the invention in a non-limiting fashion.

In an exemplary process according to the present invention, a polygraph examiner asks a subject irrelevant questions (e.g., "Do you live on 555 Main Street?"), and the response ("No") is recorded. Subsequently, control questions CQ, which are not specific to the act investigated, are asked, (e.g., "Have you ever stolen prior to working for this company?").

The subject answers "No". The response, CQR, is recorded.

The examiner then asks a relative question, RQ, "Did you take the money from the company safe?"

The subject answers, "No". The response, RQR, is recorded.

The examiner asks another control question, CQ2, "Before you were 32 years old, did you ever steal from your place of employment"?

The subject answers, "No". The response CQR2, is recorded.

The examiner asks a second relevant question, RQ2, "Did you take the $5000 from the company safe?"

The subject replies, "No". The response RQR2 is recorded.

The examiner repeats the test by asking the above questions 3 times or more, and analyzes the results manually or with the aid of a computer. If the examiner finds that responses to control questions, CQR, are greater than the responses to relevant questions, RQR, then his conclusion is a NDI, No Deception Indicated.

If, however, magnitude of responses to relevant questions, RQR, are greater than the magnitude of responses to control questions, CQR, then his conclusion is Deception Indicated, DI.

In the situation where the conclusion is NDI, or the results of the tests appear inconclusive, the use of polygraph countermeasures must be investigated. The examiner determines the average $X_C$ of time intervals 14 during the control question-answer groups and the average $X_R$ of time intervals 16 of the relevant question-answer groups.

If the examiner finds that $X_C$ substantially deviates from $X_R$ (e.g., by a pre-determined value, as described hereinabove), then the conclusion is that the subject has employed countermeasures, or "countermeasures indicated" (CI).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications mentioned in this specification are herein incorporated in their entirety by reference into the specification, to the same extent as if each individual publication was specifically and individually indicated to be incorporated herein by reference. In addition, citation or identification of any reference in this application shall not be construed as an admission that such reference is available as prior art to the present invention.

What is claimed is:

1. A method for identifying a use of countermeasures by a subject of a polygraph test, the method comprising the steps of:
   (a) posing a plurality of control questions to the subject;
   (b) posing a plurality of relevant questions to the subject;
   (c) determining, for each question of said controlling questions and said relevant questions, a rime interval between an end of said question and a start of an answer by the subject to said question, thereby generating a plurality of control question time intervals and a plurality of relevant question time intervals, and
   (d) comparing said control question time intervals to said relevant question time intervals of the subject, so as to identify the countermeasures.

2. The method of claim 1, further comprising the step of:
   (e) monitoring at least one involuntary physiological response of the subject.

3. The method of claim 1, further comprising the step of:
   (d) displaying sound waves of said answer.

4. The method of claim 1, wherein said posing of said control questions and said relevant questions transpires during the polygraph test.

5. The method of claim 1, wherein said answer is a sound response.

6. The method of claim 1, further comprising the step of:
   (e) recording a sound recording of said each question and said answer.

7. The method of claim 1, wherein, in said comparing of said time intervals, $X_C$ represents an average of said time intervals pertaining to said control questions, and $X_R$ represents art average of said time intervals pertaining to said relevant questions, and wherein the use of countermeasures by the subject is indicated when a difference between $X_C$ and $X_R$ exceeds a pre-determined value.

8. The method of claim 1, wherein, in said comparing of said time intervals, $X_C$ represents an average of said time intervals pertaining to said control questions, $X_R$ represents an average of said time intervals pertaining to said relevant questions, and $\delta_1$ and $\delta_2$ are pre-determined values, and wherein the use of countermeasures by the subject is indicated when $X_R - X_C > \delta_1$ or when $X_C - X_R > \delta_2$.

9. The method of claim 1, wherein, in said comparing of said time intervals, $X_C$ represents an average of said time intervals pertaining to said control questions, and $X_R$ represents an average of said time intervals pertaining to said relevant questions, and wherein No Deception indicated (NDI) is concluded when a difference between $X_C$ and $X_R$ is below a pre-determined value.

10. A system for detecting a use of countermeasures by a subject of a polygraph test, the system comprising:
    (a) a polygraph instrument for recording at least one involuntary physiological activity of the subject;
    (b) a sound-recording device for recording audio data during the polygraph test;
    (c) a time-measuring device for producing time information, and
    (d) a processing unit operatively connected to said sound-recording device and to said time-measuring device, wherein said processing unit is designed and configured to utilize said time information and said audio data so as to:
       (i) calculate for each question of a plurality of questions, a physiological response time between a time associated with said question and a change in said physiological activity, thereby generating a plurality of said physiological response times, and
       (ii) process said physiological response times to identify the countermeasures.

11. The system of claim 10, wherein said at least one involuntary physiological activity is monitored using a galvanic skin response (GSR).

12. The system of claim 10, wherein said change in said physiological activity corresponds to a minimum value adjacent to a galvanic skin response peak to said question.

13. The system of claim 10, wherein said time associated with said question is a beginning of said question.

14. The system of claim 10, wherein said plurality of questions includes a plurality of control questions a plurality of relevant questions, and wherein said plurality of physiological response times includes a plurality of control question physiological response times and a plurality of relevant question physiological response times.

15. The system of claim 14, wherein said processing unit is designed and configured to compare said control question physiological response times and a said relevant question physiological response times to identify the countermeasures.

16. The system of claim 15, wherein said time associated with said question is a beginning of said question.

17. The system of claim 15, wherein said at least one involuntary physiological activity is monitored using a galvanic skin response (GSR).

18. The system of claim 15, wherein said change in said physiological activity corresponds value adjacent to a response peak of said physiological activity.

19. The system of claim 18, wherein said physiological activity is monitored using a galvanic skin response (GSR).

* * * * *